United States Patent [19]
Joseph

[11] Patent Number: 6,117,430
[45] Date of Patent: Sep. 12, 2000

[54] FLOWABLE DRUG PRECURSOR PRODUCTS READY FOR PRESSING FOR TABLETS, PELLETS AND SUGAR-COATED TABLETS AND PROCESSES FOR PREPARING THE SAME

[75] Inventor: Heinz Walter Joseph, Berg, Germany

[73] Assignee: Bionorica Arzneimittel GmbH, Neumarkt, Germany

[21] Appl. No.: 09/219,035

[22] Filed: Dec. 23, 1998

[30] Foreign Application Priority Data

Dec. 15, 1998 [DE] Germany .................. 198 57 816

[51] Int. Cl.⁷ .................................. A01N 65/00
[52] U.S. Cl. ............... 424/195.1; 424/451; 424/464; 424/489
[58] Field of Search ................ 424/195.1, 489, 424/451, 464

[56] References Cited

U.S. PATENT DOCUMENTS

| | | | |
|---|---|---|---|
| 3,843,788 | 10/1974 | Iwasa et al. | 424/195.1 |
| 4,321,263 | 3/1982 | Powell et al. | 424/195.1 |
| 4,842,859 | 6/1989 | Liu | 424/195.1 |
| 5,204,101 | 4/1993 | Stubblefield et al. | 424/195.1 |
| 5,277,910 | 1/1994 | Hidvegi | 424/195.1 |
| 5,422,346 | 6/1995 | Mitchell et al. | 514/54 |
| 5,939,071 | 8/1999 | Joseph | 424/195.1 |

OTHER PUBLICATIONS

Desopharmex Product Brochure—last modified Jul. 17, 1998, one page.
Darya–Varia—Annual Report, 1994.
Darya–Varia—Prospectus—Rights Issue, 1996.
*Pilot–Vacuum Dryer*, INOX Glatt AG.
*Vacuum Dryers*, INOX Glatt AG.

*Primary Examiner*—Christopher Tate
*Attorney, Agent, or Firm*—Ratner & Prestia

[57] ABSTRACT

The present invention relates to a process for making a flowable drug precursor product ready for pressing comprising humidifying dried plant drug material in a vacuum drying device together with the desired additives, carriers and/or excipients, which device comprises a multi-blade stirrer having its own drive and extending through a cylindrical mixing and drying chamber, said device optionally being provided with a filter, a back-purge means, a solvent condenser with an after-cooler and a collection vessel, a back-condenser and/or a process, control and regulation unit, and drying the humid mixture at a jacket temperature of the device of 20 to 50° C., a product temperature between 20 and 45° C. and a pressure of 20 to 500 mbar to obtain the precursor product, and also relates to said precursor products as such.

2 Claims, 1 Drawing Sheet

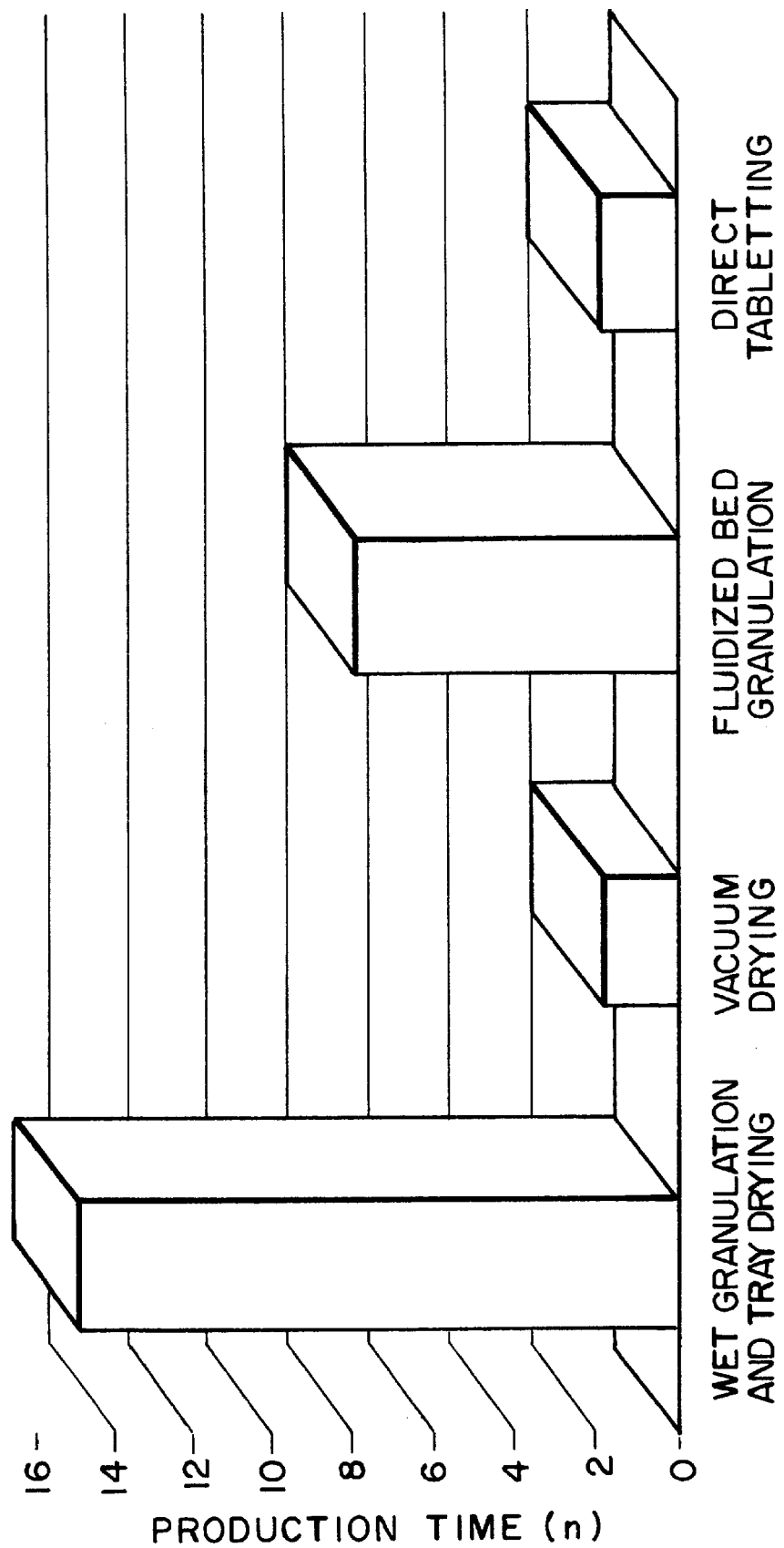

FLOWABLE DRUG PRECURSOR PRODUCTS READY FOR PRESSING FOR TABLETS, PELLETS AND SUGAR-COATED TABLETS AND PROCESSES FOR PREPARING THE SAME

The present invention relates to a process for making flowable drug precursor products ready for pressing for the preparation of tablets, sugar-coated tablets and pellets from plant drugs, said precursor products being suitable for tabletting without additional interim steps, and the drug precursor products as such. In particular, it relates to a process which avoids the disadvantages of conventional wet granulation without having to resort to direct tabletting.

Conventional processes for making tablets from dried plant drugs are wet granulation on the one hand and direct tabletting on the other. Since direct tabletting requires the use of pre-treated or pre-granulated substances and excipients and carriers subjected to similar pre-treatment, wet granulation is usually chosen for cost reasons. In this process, the active ingredients, i.e. the dried plant drugs and optional excipients are humidified, mixed in the humid state, for example by kneading, stirring etc., and the mixture then subjected to granulation. In order to obtain a granulate suitable for tabletting, any water contained after wet granulation must be removed. The drying time in the classical process of tray drying is approx. 15 hours during which time the plant drugs are exposed to oxidation by oxygen in the air. The drying temperature of the material is between 65° C. and 75° C., which may disadvantageously influence the active ingredients contained therein. In addition, the long drying time and the use of non-sterile plant material often result in the development of undesirable germs such as mould cultures, because their growth is favoured by such system conditions.

On the other hand, the limits for the germ count of plant drugs containing such materials have been determined in DAB 98 (German Pharmacopoeia, $10^{th}$ edition). Even though they would be appropriate for use under chemical and pharmaceutical aspects, the drugs must often be discarded, because they do not comply with the strict requirements of the pharmacopoeias. In order to stay within the germ count limit, DE-A-195 47 973, for example, has proposed to sterilise plant drugs before wet granulation by a specific process in a vacuum drying system comprising a multi-blade stirrer under reduced pressure conditions and thus to reduce the initial germ count of the material used for wet granulation. The smaller the initial germ count, the smaller the germ count of the granulate obtained after the main drying step and suitable for tabletting. However, this process does not reduce the drying time so that the exposure to oxygen in the air remains unchanged.

Even the shorter drying process by means of a fluidised-bed apparatus requires between 7 and 8 hours with incoming air being preheated to 65° C. At the same time, large volumes of air are required (3,000 to 5,000 $cm^3$/h). Thus, fluidised-bed shift-batch production requires between 21,000 and 40,000 $cm^3$ of pre-heated air. On the other hand, it has been proven that air and particularly heated air has a detrimental influence on the contents of flavonoids, essential oils, polyphenols and unsaturated fatty acids which are especially susceptible to oxidation by oxygen contained in the air. Therefore, intensive exposure is undesirable. In addition, even drying by the fluidised-bed system cannot prevent proliferation of aerobic germs in view of the lengthy drying time of 7 to 8 hours, so that this process also encounters the above-mentioned problems.

For direct tabletting, the second process known in the prior art for making tablets from dried plant drugs, the individual tablet components, i.e. the drug material and the carriers or excipients, respectively, must be provided in a form suitable for direct tabletting, e.g. as a granulate, and require lengthy mixing in this form. Since, in addition to the active ingredients, the finished tablets sometimes may contain up to 20 different substances which must be introduced at a strictly defined location in the production process to insure that the newly added ingredients remain stable in the granulate, direct tabletting is a comparatively complicated method. Therefore, granulation is a lengthy and costly process in the pharmaceutical industry which binds time, energy and technical personnel to an undesirable extent.

Therefore, it is the objective of the present invention to provide a fast and simple process which permits preparation of a flowable drug precursor product ready for pressing without requiring a lot of time, energy and staff, but which is effective with regard to the product compatibility of the individual ingredients and excipients, does not negatively influence the plant ingredients and achieves an adequate germ count.

The objective of the invention is achieved by a process for making a flowable drug precursor product ready for pressing comprising humidifying dried plant drug material in a vacuum drying device together with the desired additives, carriers and/or excipients, which device comprises a multi-blade stirrer having its own drive and extending through a cylindrical mixing and drying chamber, said device optionally being provided with a filter, a back-purge means, a solvent condenser with an after-cooler and a collection vessel, a back-condenser and/or a process, control and regulation unit, and drying the humid mixture at a jacket temperature of the device of 20 to 50° C., preferably 20 to 40° C. and most preferably 30° C., a product temperature between 20 and 40° C., preferably 20° C. to 30° C. and most preferably 20 to 25° C. and a pressure of 20 to 500 mbar, preferably 50 to 200 mbar and most preferably 50 to 100 mbar to obtain the precursor product.

Examples for commercial vacuum drying devices which may be used in the process according to the invention are the ITUT-INOX® universal dryers, e.g. the types ITUT 20, ITUT 50, ITUT 100 or ITUT 2000.

The desired components of the finished tablet or the drug preparation, respectively, may be introduced into the process either simultaneously or consecutively. By simultaneously mixing and drying the components with the aid of the multi-blade stirrer, much less humidity needs to be added to the wet granulate than in the conventional wet granulation process. Preferably, humidification is effected by adding water or a water/solvent mixture in an amount of 0.01 to 0.05 ml/g solids, preferably 0.02 to 0.04 ml/g solids. Preferred solvents are lower alcohols such as methanol, ethanol, propanol or glycol and glycerol, ketones such as acetone, or ethers such as diethyl ether, glyme and diglyme. Water or water/alcohol mixtures are preferred. In addition, highly dispersed silica in an amount of 1 to 10%, preferably 3 to 6%, based on the total amount is preferably added.

Owing to the lower degree of humidification, it is possible to decrease the drying time to 30 minutes to 2 hours, preferably 1 to 1.5 hours. Since, in addition to the decrease in drying time which results in a considerable reduction in the germ count, the drying temperature and the air blown in may be reduced, the flowable, ready-for-pressing precursor products according to the invention have a higher content of active ingredients in comparison with wet granulates prepared by conventional methods. This is due to the fact that the undesirable effects of air drying may be eliminated. The process according to the invention provides the additional advantage that the time for making the granulate may be reduced significantly, the production process is simplified and that far less personnel is required.

FIG. 1 shows a time comparison between classical wet granulation, fluidised-bed granulation and vacuum granulation according to the invention as well as direct tabletting. This illustration shows that the process according to the invention is comparable to direct tabletting with regard to the time advantage. Direct tabletting, however, is far more complicated and places much higher requirements on the purity and physical characteristics of the starting materials used. On the whole, the process according to the invention thus offers advantages vis-à-vis all other processes of the prior art.

The dried plant material that may be used according to the invention is a material of blossoms, roots, rhizomes, bulbs, leaves and other parts of the desired plant. For the drugs species of althaeae, juglans, millefolium, centaurium, rosmarinum, gentiana, primula, rumex, sambuco, echinacea, phyllanthus and verbena as well as agnus castus, allium, especially allium cepa, hedera helix, hippocastanus, curcuma, galphimia, especially galphimia glauca, herba thymii or mixtures thereof may be mentioned. Especially preferred are flos sambuci, flos primulae, herba rumicis, radix gentianae, herba verbenae and mixtures thereof, for example the mixtures used for making Sinupret® or Sinupret® forte sugar-coated tablets. Sinupret® is a known pharmaceutical for treating acute and chronic inflammation of the paranasal sinus and the respiratory tract.

Carriers, additives and excipients which may be employed according to the invention are those customarily used for tabletting. Special mention may be made of starch and starch derivatives, silica, lactose, lactose monohydrate, cellulose and cellulose derivatives, magnesium stearate, calcium stearate, calcium hydrogen phosphate, PVP or povidone, polyethylene glycol or Macrogol, mannitol, sorbitol, gelatine, sugar alcohols, stearic acid and its salts as well as mixtures thereof. Silica either alone or admixed with one or several of the above substances is preferred. Special mention may be made of acryl derivatives, alginic acid, α-octadecyl-Ω-hydroxypoly-(oxyethylen)-5-sorbic acid-$H_2O$, gum arabic, flavouring substances, ascorbic acid, calcium carbonate, calcium hydrogen phosphate, calcium phosphate, calcium stearate, carmellose sodium, cellulose, cellulose derivatives, dimeticon, colouring agents, gelatine, glucose syrup, highly dispersed silica, hypromellose, potassium benzoate, lactose monohydrate, Macrogol, magnesium carbonate, magnesium oxide (light), magnesium stearate, corn starch, corn swelling starch, mannite, mannitol, mono- and diglyceride of edible fatty acids, montan glycol wax, sodium benzoate, (anhydrous) sodium carbonate, sodium chloride, sodium hydrogen carbonate, poly(butylmethacrylate)-co-(2-dimethyl amino ethyl methacrylate), polyvidone K25, povidone, refined castor oil, sucrose, sucrose monostearate, shellac, sorbitol, starch, starch derivatives, stearic acid, talcum, titanium dioxide and tartaric acid.

The precursor product thus obtained may be compressed to tablets, sugar-coated tablets or pellets of the desired size and density without additional interim steps. Afterwards, these tablets may be provided with coatings, covers etc. by conventional processes. The precursor product may also be filled as such into capsules, for example hard or soft gelatine capsules, filled directly into other individually packed forms or formulated as powder/granulate.

Composition Examples

1. Sinupret® Sugar-coated Tablets

Composition

| 1. | Active ingredients | Amount |
|---|---|---|
| | Gentian root (powdered) | 6,000 mg |
| | Primula blossoms with calyx (powdered) | 18,000 mg |
| | Sorrel leaves (powdered) | 18,000 mg |
| | Verbena leaves (powdered) | 18,000 mg |
| | Elder blossoms (powdered) | 18,000 mg |

2. Other Possible Ingredients

Acryl derivatives, alginic acid, α-octadecyl-Ω-hydroxypoly-(oxyethylene)-5-sorbic acid-$H_2O$, gum arabic, flavouring agents, ascorbic acid, calcium carbonate, calcium hydrogen phosphate, calcium phosphate, calcium stearate, carmellose sodium, cellulose, cellulose derivatives, dimeticon, colouring agents, gelatine, glucose syrup, highly dispersed silica, hypromellose, potassium benzoate, lactose monohydrate, Macrogol, magnesium carbonate, magnesium oxide (light), magnesium stearate, corn starch, corn swelling starch, mannite, mannitol, mono and diglyceride of edible fatty acids, montan glycol wax, sodium benzoate, (anhydrous) sodium carbonate, sodium chloride, sodium hydrogen carbonate, poly(butylmethacrylate)-co-(2-dimethyl amino ethyl-methacrylate), polyvidone K25, povidone, refined castor oil, sucrose, sucrose monostearate, shellac, sorbitol, starch, starch derivatives, stearic acid, talcum, titanium dioxide and tartaric acid.

2. Sinupret® Forte Sugar-coated Tablets

Composition

| 1. | Active ingredients | Amount |
|---|---|---|
| | Gentian root (powdered) | 12,000 mg |
| | Primula blossoms with calyx (powdered) | 36,000 mg |
| | Sorrel leaves (powdered) | 36,000 mg |
| | Verbena leaves (powdered) | 36,000 mg |
| | Elder blossoms (powdered) | 36,000 mg |

2. Other Possible Ingredients

Acryl derivatives, alginic acid, α-octadecyl-Ω-hydroxypoly-(oxyethylene)-5-sorbic acid-$H_2O$, gum arabic, flavouring agents, ascorbic acid, calcium carbonate, calcium hydrogen phosphate, calcium phosphate, calcium stearate, carmellose sodium, cellulose, cellulose derivatives, dimeticon, colouring agents, gelatine, glucose syrup, highly dispersed silica, hypromellose, potassium benzoate, lactose monohydrate, Macrogol, magnesium carbonate, magnesium oxide (light), magnesium stearate, corn starch, corn swelling starch, mannite, mannitol, mono and diglyceride of edible fatty acids, montan glycol wax, sodium benzoate, (anhydrous) sodium carbonate, sodium chloride, sodium hydrogen carbonate, poly(butylmethacrylate)-co-(2-dimethyl amino ethyl-methacrylate), polyvidone K25, povidone, refined castor oil, sucrose, sucrose monostearate, shellac, sorbitol, starch, starch derivatives, stearic acid, talcum, titanium dioxide and tartaric acid.

Production Process

The active drug ingredients and the other ingredients of the core mass were humidified with 0.3 l of water (for a 10 kg batch) in an INOX-Glatt-Maurer device at a jacket temperature of the device of 30° C., a product temperature of between 20 and 45° C. and a pressure of 100 mbar and then dried within one hour. After that, the product according to the invention was mixed with stearic acid and the flowable mixture ready for pressing compressed into tablets. These tablets were provided with a sugar coating according to conventional processes.

Since the drying time of one hour is much shorter than the 15 hours required for the classical wet granulation process, the process according to the invention provides significant advantages compared with the wet granulation process with regard to the volume of the throughput.

What is claimed is:

1. A flowable drug precursor product ready for pressing obtained by humidifying, with one of water or a water/solvent mixture in an amount of from 0.01 to 0.05 ml/g solids added to a dried plant material together with desired additives, carriers and/or excipients in a vacuum drying device comprising a multi-blade stirrer extending through a cylindrical mixing and drying chamber and having its own drive, and drying the humid mixture at a jacket temperature of the device of 20 to 50° C., a product temperature of 20 to 45° C. and a pressure of 20 to 500 mbar for between 30 minutes and 2 hours until the flowable drug precursor product is obtained.

2. A flowable drug precursor product ready for pressing according to claim 1, wherein the dried plant material used is a mixture of powdered sorrel leaves, powdered verbena leaves, powdered gentian root, powdered elder blossoms and powdered primulae.

* * * * *